(12) United States Patent
Daniel et al.

(10) Patent No.: US 9,320,539 B2
(45) Date of Patent: Apr. 26, 2016

(54) SURGICAL SYSTEM FOR AND A METHOD OF DISSECTION OF TISSUE AWAY FROM AN ORGAN OR BODY LUMEN

(71) Applicant: Coloplast A/S, Humlebaek (DK)

(72) Inventors: Geoffrey A. Daniel, Crystal, MN (US); Fernando El-Hage, Brooklyn Park, MN (US); Neal Poucher, North Oaks, MN (US)

(73) Assignee: Coloplast A/S, Humlebaek (DK)

( * ) Notice: Subject to any disclaimer, the term of this patent is extended or adjusted under 35 U.S.C. 154(b) by 77 days.

(21) Appl. No.: 14/254,045

(22) Filed: Apr. 16, 2014

(65) Prior Publication Data

US 2015/0094695 A1 Apr. 2, 2015

Related U.S. Application Data

(60) Provisional application No. 61/884,146, filed on Sep. 30, 2013.

(51) Int. Cl.
*A61M 27/00* (2006.01)
*A61B 17/3205* (2006.01)
(Continued)

(52) U.S. Cl.
CPC .............. *A61B 17/3205* (2013.01); *A61B 17/28* (2013.01); *A61B 17/3201* (2013.01); *A61B 17/52* (2013.01); *A61B 2017/00367* (2013.01); *A61B 2017/00876* (2013.01); *A61B 2017/320044* (2013.01); *A61B 2017/320052* (2013.01); *A61B 2019/2253* (2013.01); *A61B 2019/448* (2013.01); *A61B 2019/481* (2013.01); *A61B 2019/4805* (2013.01); *A61M 25/00* (2013.01); *A61M 25/0017* (2013.01); *A61M 25/0043* (2013.01); *A61M 2025/0008* (2013.01)

(58) Field of Classification Search
CPC ............... A61B 17/28; A61B 17/3201; A61B 2017/00876; A61B 2017/320044; A61B 2019/481; A61B 17/3205; A61B 17/52; A61B 2017/00367; A61B 2017/320052; A61M 25/00; A61M 25/0017
USPC .................................. 604/544; 600/104, 106
See application file for complete search history.

(56) References Cited

U.S. PATENT DOCUMENTS

2007/0239170 A1* 10/2007 Brock ................ A61B 17/0469
606/108
2009/0093836 A1 4/2009 Feld
(Continued)

FOREIGN PATENT DOCUMENTS

DE 102011005338 A1 9/2012

*Primary Examiner* — Jacqueline Stephens
*Assistant Examiner* — Andrew J Mensh
(74) *Attorney, Agent, or Firm* — Coloplast Corp., Coloplast A/S; Nick Baumann

(57) ABSTRACT

A surgical system adapted for dissection of tissue away from a body lumen includes a tissue dissection tool and a catheter. The tissue dissection tool includes a shaft connected between a handle and a tissue dissection head. At least the tissue dissection head of the tissue dissection tool is magnetized to a first polarity. The catheter is insertable into a urethra, with a wall of the catheter magnetized to the first polarity. When the catheter is inserted into the urethra, the first polarity of the catheter is configured to repel the first polarity of the tissue dissection head of the tool away from the catheter and away from in the urethra.

11 Claims, 14 Drawing Sheets

(51) Int. Cl.
*A61B 17/28* (2006.01)
*A61B 17/3201* (2006.01)
*A61B 17/52* (2006.01)
*A61B 1/00* (2006.01)
*A61B 19/00* (2006.01)
*A61M 25/00* (2006.01)
*A61B 17/00* (2006.01)
*A61B 17/32* (2006.01)

(56) References Cited

U.S. PATENT DOCUMENTS

| | | | |
|---|---|---|---|
| 2010/0087798 A1 | 4/2010 | Adams | |
| 2010/0168561 A1* | 7/2010 | Anderson | A61B 17/3403 600/424 |
| 2010/0222664 A1* | 9/2010 | Lemon | A61M 25/09 600/409 |
| 2010/0240952 A1 | 9/2010 | Okazaki et al. | |

\* cited by examiner

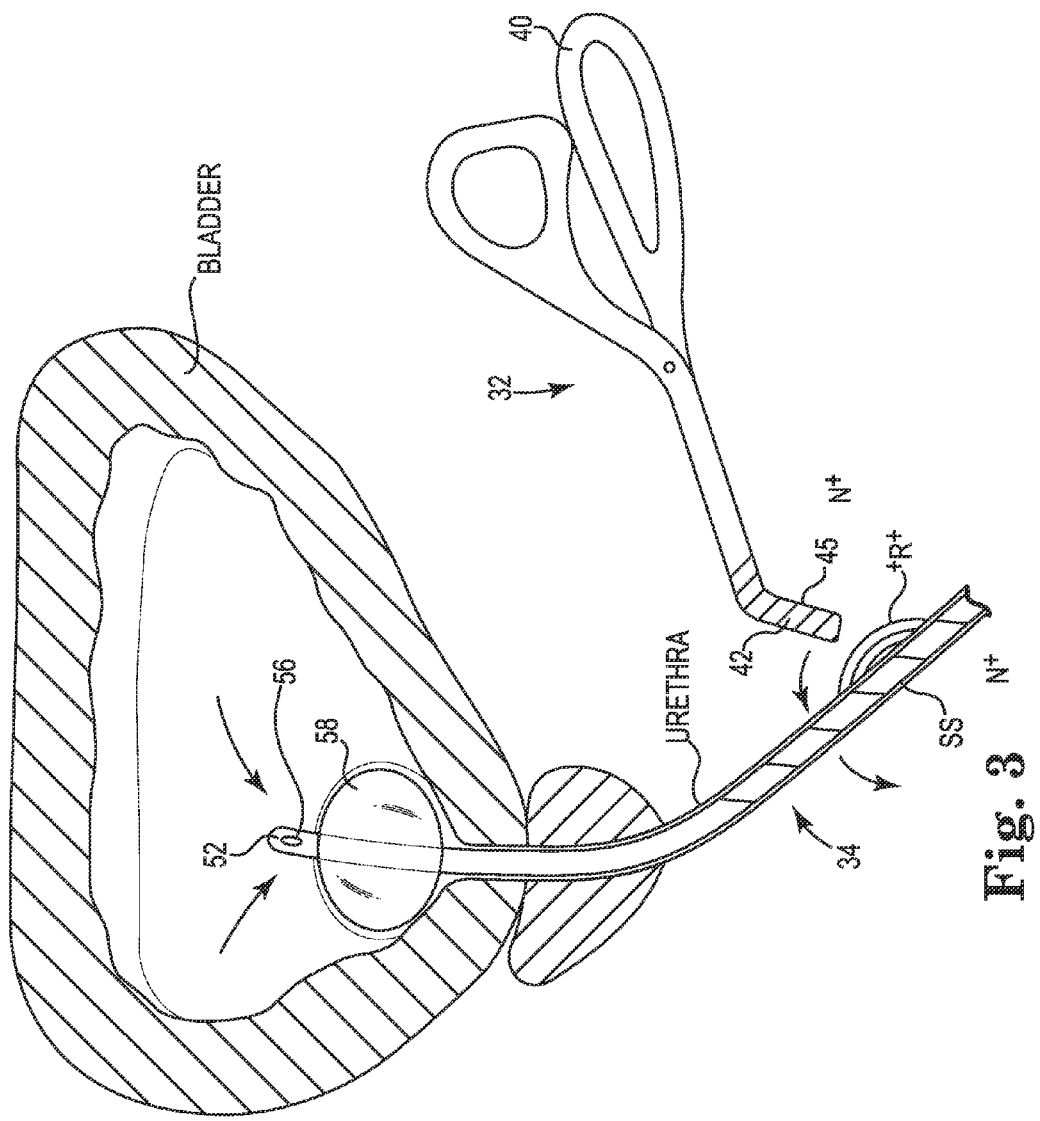

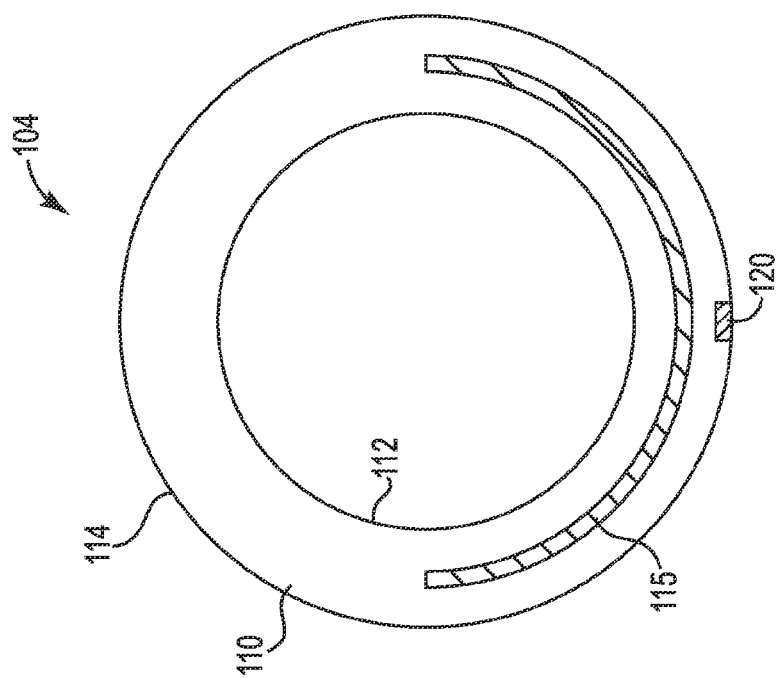
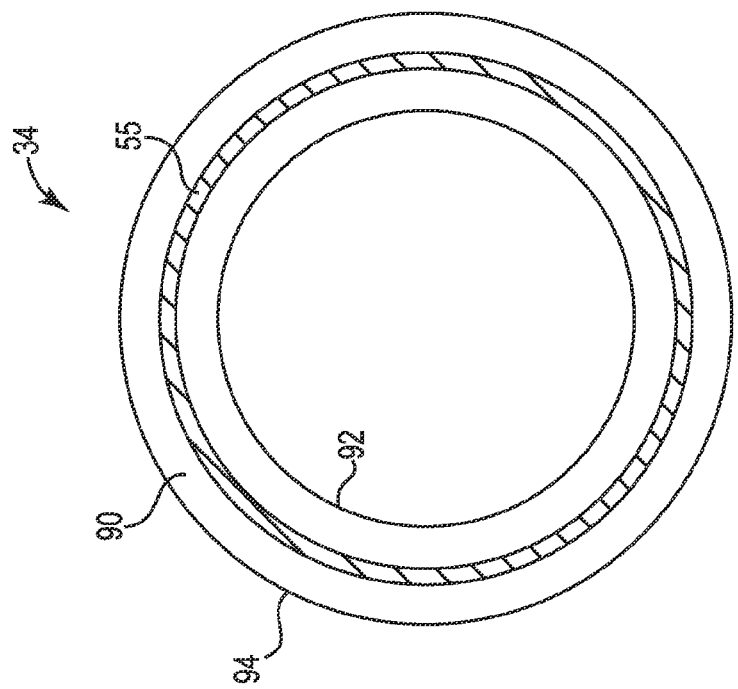

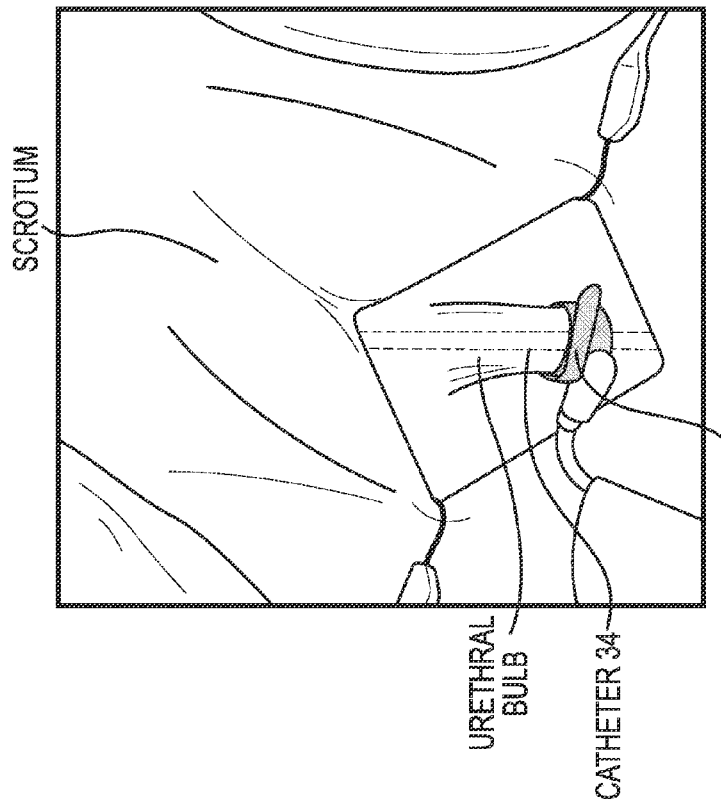
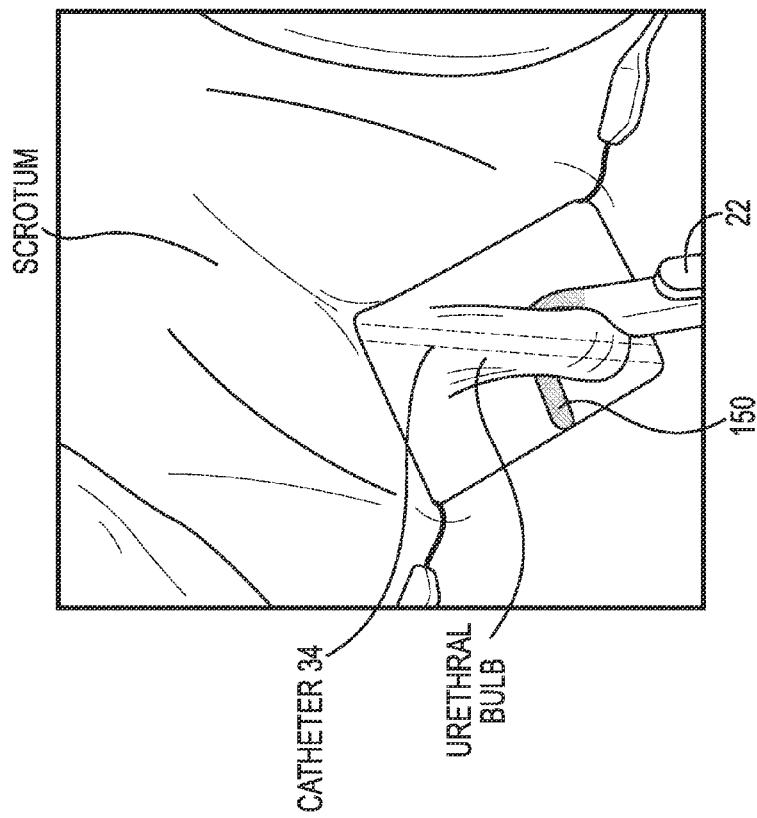

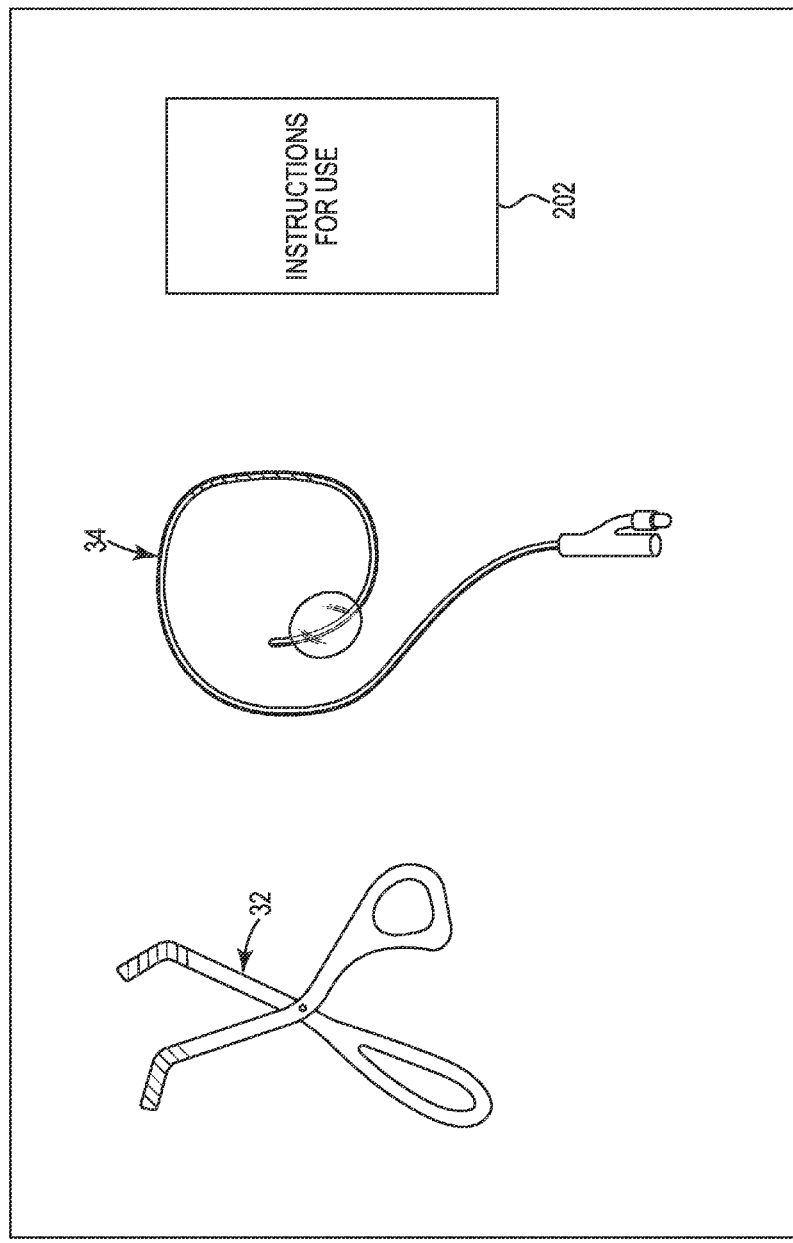

SURGICAL SYSTEM FOR AND A METHOD OF DISSECTION OF TISSUE AWAY FROM AN ORGAN OR BODY LUMEN

BACKGROUND

Urinary incontinence affects about 200 million people worldwide and about 25 million people in the US. Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

One aspect provides a surgical system adapted for dissection of tissue around an organ or around a lumen. The surgical system includes a tissue dissection tool and a catheter. The tissue dissection tool includes a shaft connected between a handle and a tissue dissection head. At least the tissue dissection head of the tissue dissection tool is magnetized to a first polarity. The catheter is insertable into the organ or the lumen, with a wall of the catheter magnetized to the first polarity. When the catheter is inserted into the organ or the lumen, the first polarity of the catheter is configured to repel the first polarity of the tissue dissection head of the tool away from the catheter and away from in the urethra.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 is a perspective view of one embodiment of a surgical system operable to dissect tissue away from a blind posterior location of the patient.

FIG. 5A is a cross-sectional view of one embodiment of a catheter of a surgical system.

FIG. 5B is a cross-sectional view of one embodiment of a catheter of a surgical system.

FIGS. 6-14 are schematic views of embodiments of the implantation of an AUS system in the urogenital region of the patient assisted by the surgical system illustrated in FIG. 3.

FIG. 15 is a top view of one embodiment of a kit of parts including a catheter, a dissection tool, and instructions for use.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this specification are suited for combination with each other, unless specifically noted otherwise.

Tissue includes soft tissue, which includes dermal tissue, sub-dermal tissue, ligaments, tendons, or membranes. As employed in this specification, the term "tissue" does not include bone.

As employed in this specification, the term "end" means endmost or the very end point of the subject being described, and the term "end portion" means that segment that is immediately adjacent to the end of the subject being described.

Figure 1:
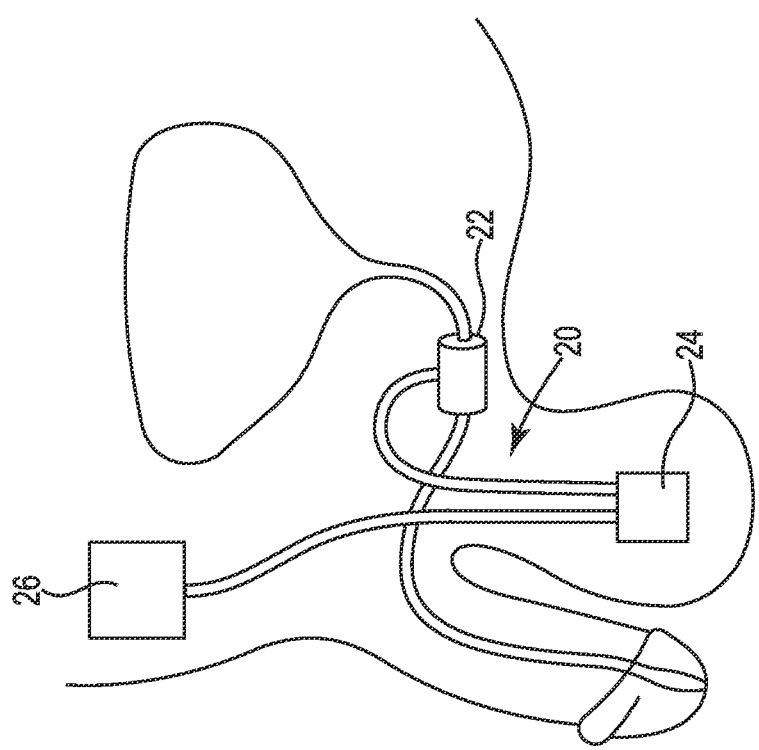
FIG. 1 is a perspective view of a prior art artificial urinary sphincter (AUS) system implanted in the urogenital region of a male patient.

FIG. 1 is a perspective view of a prior art artificial urinary sphincter (AUS) system 20 implanted in the urogenital region of a male patient. The AUS system 20 includes three components cooperatively attached with kink-resistant tubing: an occlusive cuff 22, a control pump 24, and a pressure-regulating balloon reservoir 26. The cuff 22 is implanted around the urethra. The control pump 24 is implanted in the scrotum of a male user. The pressure-regulating balloon reservoir 26 is implanted in the prevesical space, for example somewhere in the abdomen. During implantation of the urinary control system 20, the surgeon will dissect tissue around the circumference of the urethra in order to create a space that allows placement of the cuff 22 around the urethra. The surgeon is usually able to visualize the anterior area of the urethra (that is, the front facing area in the line of sight of the surgeon) for about 180-210 degrees around the anterior urethra. The posterior portion of the urethra is not visible to the surgeon, as it is not in the line of sight of the surgeon. For this reason, some surgeons call the dissection of tissue away from the posterior portion of the urethra a "blind" dissection. Surgeons are exceedingly cautious when dissecting tissue away from and around the urethra to avoid the undesirable outcome of cutting into the urethra.

Embodiments described in this application provide a surgical system and a method for dissection of tissue away from the entire circumference around the urethra or other organ or lumen. The surgical system includes a tissue dissection tool and a catheter, where both the tool and the catheter are magnetized to have the same polarity. Thus, when the catheter is inserted into the urethra, the polarity of the catheter repels the tissue dissection head because the cutting head is at the same polarity as the catheter. In other words, these two components are configured to magnetically repel—or push away—from one another. Thus, when the surgeon is conducting a blind dissection of the tissue around the urethra, the surgical system of this application provides increased assurance that the tissue dissection head will be pushed away from the posterior side of the urethra.

Figure 2:
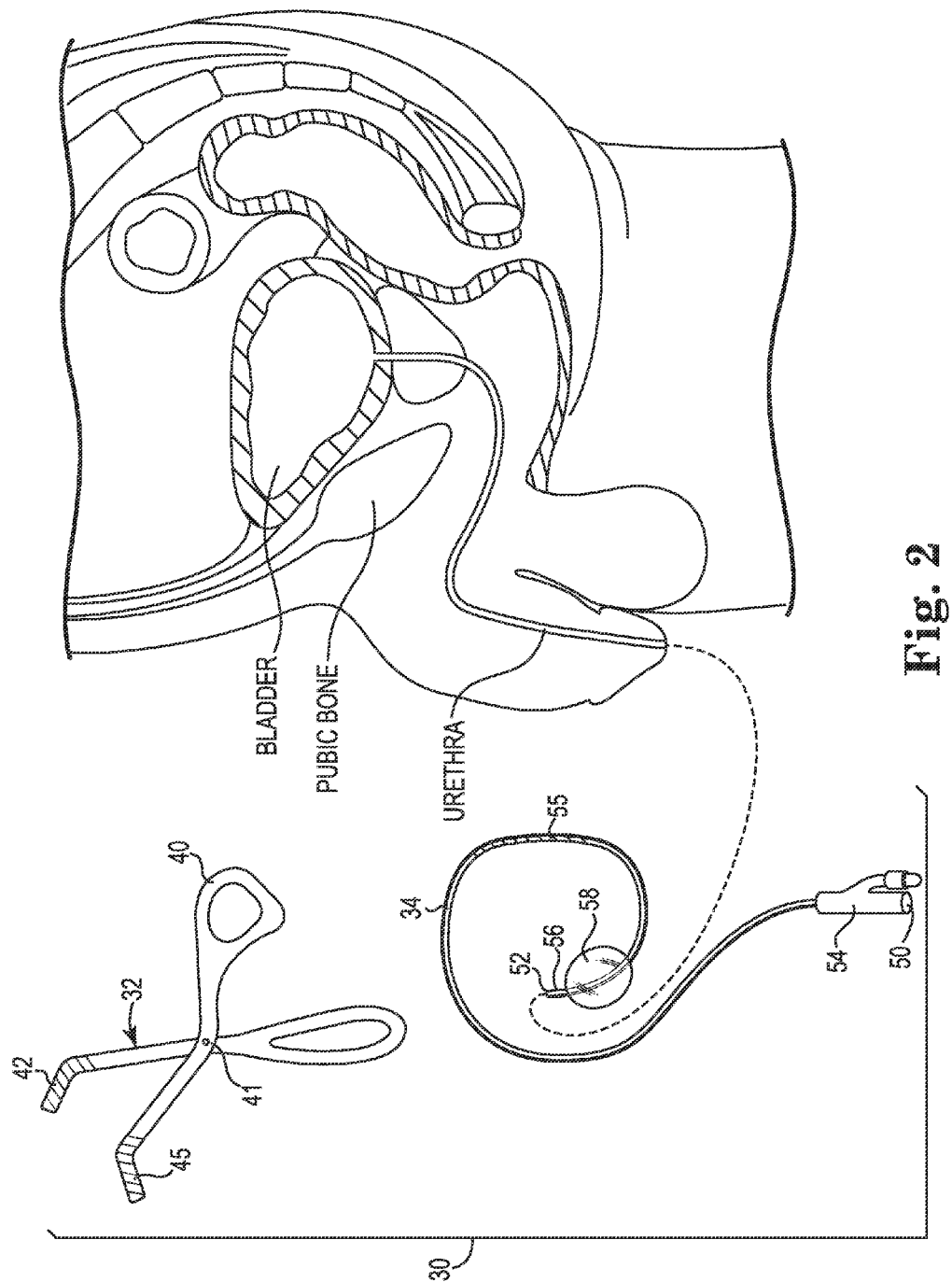
FIG. 2 is a schematic view of one embodiment of a surgical system operable to place a cuff of an AUS system into a patient.

FIG. 2 is a perspective view of one embodiment of a surgical system 30 including a tissue dissection tool 32 and a catheter 34.

The tissue dissection tool 32 (tool 32) includes a shaft 41 connected between a handle 40 and a cutting surface 42 (or dissection head 42) that is located opposite of the handle 40. The tool 32 is suitably provided as a single blade cutting tool, scissors-like tool provided with cutting shears, or other tool that is suitably configured to dissect pelvic tissue around the urethra. One suitable tool 32 includes a right angle dissection tool with the cutting surface 42 oriented at about 90 degrees relative to the shaft attached to the handle 40. It is acceptable to have the dissection head 42 oriented in a range between 10-80 degrees relative to the shaft attached to the handle 40. At least a portion 45 of the tool 32 is magnetized at a first polarity. For example, in one embodiment the cutting surface 42 is magnetized at a polarity that is the same polarity as a polarity of a magnetized portion of the catheter 34, such that the cutting surface 42 is configured to magnetically repel away from the catheter 34.

It is acceptable to magnetize the entire tool 32 at a single polarity. In one embodiment, the handle 40 of the tool 32 is fabricated from a surgical steel or other metal acceptable to the surgical suite and the portion 45 of the tool 32 that is magnetized is fabricated from a rare earth magnet. For example, the magnetized portion 45 is provided as a rare earth magnet and integrated to the handle 40. Rare earth magnets are permanent magnets that are formed from the lanthanide elements of metals with ferromagnetic properties. Rare earth magnets are characterized as having a magnetic strength of 2-5 times greater than ferrite magnets.

The catheter 34 is configured for insertion into the urethra of the patient. The catheter 34 includes a lumen 50 that is sized and configured to transport urine from the bladder. The lumen 50 extends from a distal end 54 of the catheter 34 (which remains outside of the patient/urethra) to a proximal end 52 of the catheter 34 that is insertable into the urethra. At least a portion 55 of the catheter 34 is magnetized to the first polarity, or the same polarity as the magnetic field of the tool 32. It is desirable that the portion 55 of the catheter 34 that is magnetized to the first polarity is or becomes located in an area of the bulbar urethra when the catheter is inserted into the urethra. The magnetized portion 55 is fabricated from one of a ferromagnet or a rare earth magnet. The proximal end 52 of the catheter 34 includes an opening 56 that allows urine to enter the catheter 34. The distal end 54 of the catheter 34 includes a connector that is attachable to a bag that is provided to collect the urine flowing from the bladder.

In one embodiment, the catheter itself is not magnetized and instead a rod of magnetic metal is directed into the catheter lumen. The magnetized rod is magnetized to the first polarity, or the same polarity as the magnetic field of the tool 32. The magnetized rod is inserted into the patient to the area of the bulbar urethra. In this manner, the magnetized rod will repel the tool 32 away from the bulbar urethra during tissue dissection.

The catheter 34 is suitably configured as a single use catheter, an indwelling catheter, or a modified Foley catheter. For example, one embodiment of the catheter 34 includes an inflatable balloon 58 located near the proximal end 54. The inflatable balloon 58 is sized to be inflated after the catheter 34 is introduced through the urethra and into the bladder. Inflation of the inflatable balloon 58 enlarges the end region of the catheter 34, which prevents the catheter 34 from undesirably sliding out of the urethra.

The catheter 34 includes a lumen 50 to transport urine. It is within the scope of this disclosure to include a catheter having a magnetized portion configured to repel the cutting surface 42 of the tool 32, where the catheter is a magnetized and flexible rod that does not transport urine. For example, given the duration of the surgery, it is acceptable if the magnetized catheter is inserted into the urethra to support and expand the urethra without having a lumen to transport urine.

FIG. 3 is a schematic view of the tool 32 deployed in cooperation with the catheter 34. The catheter 34 has been inserted into the urethra and the inflatable balloon 58 has been expanded to maintain the catheter 34 in the bladder. The tissue around and in the area of the urethra is not illustrated to allow better visualization of the tool 32.

The portion 45 of the tool 32 is magnetized to the first polarity (N) and the portion 55 of the catheter 34 is also magnetized to the same first polarity (N). The magnetic field of the portion 55 of the catheter 34 inside the urethra is adapted to repel +R+ the magnetized portion 45 of the tool 32. This aspect is particularly useful as the cutting surface 42 is directed posterior of the urethra. In this manner, the cutting surface 42 of the tool 32 is pushed away from the urethra as the surgeon dissects the tissue posterior to the urethra, which allows the surgeon to dissect tissue that is out of his/her field of view.

Figure 4C:
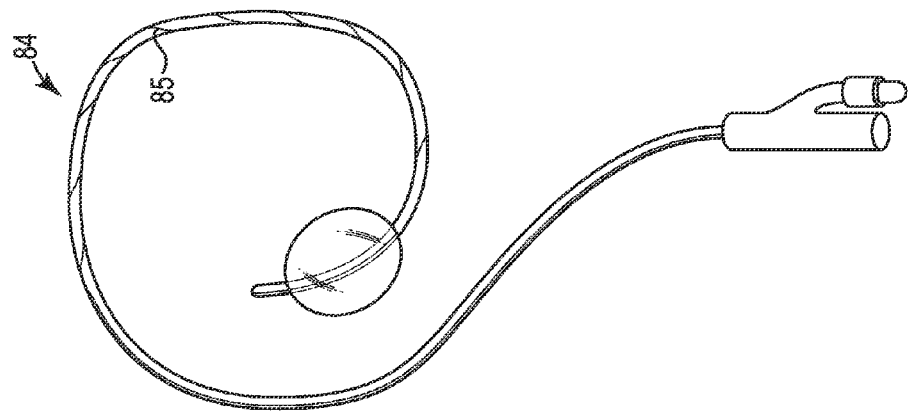
FIG. 4A-FIG. 4C are embodiments of a catheter of a surgical system operable to place a cuff of an AUS system into a patient.
Figure 4B:
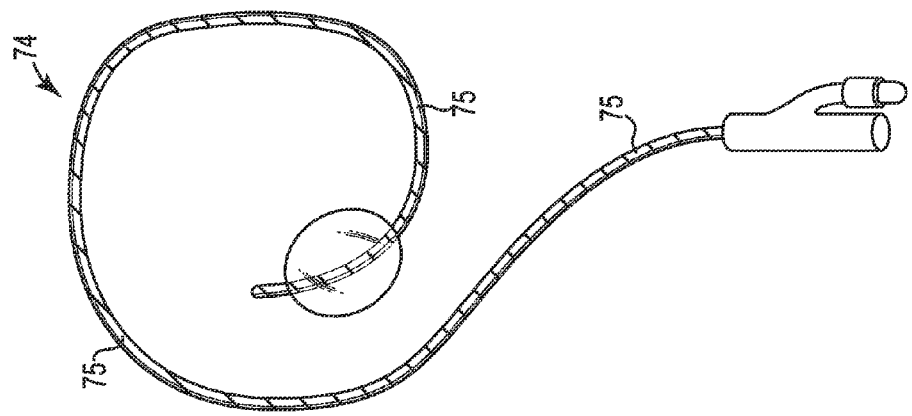
Figure 4A:
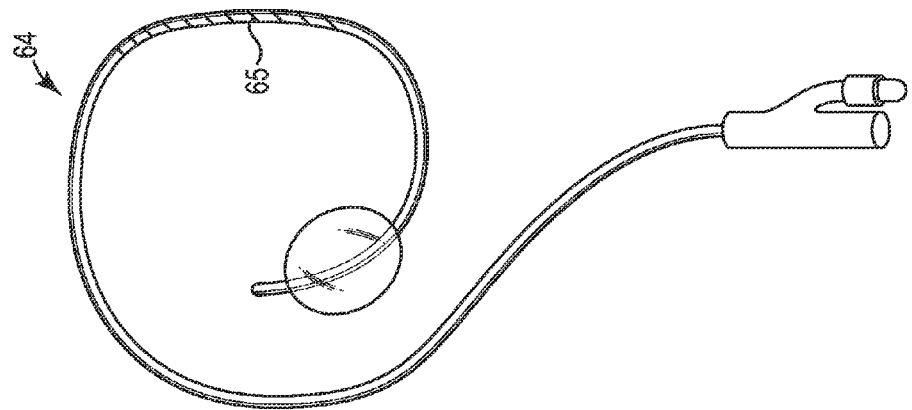

FIGS. 4A-4C are perspective views of embodiments of catheters.

FIG. 4A is a perspective view of a catheter 64 including one discrete portion 65 that is magnetized at the same polarity as the tool 32. The magnetized portion 65 is located between the proximal and distal ends of the catheter, for example over only an extent that is less than about 50% of the length of the catheter. The magnetized portion 65 includes an embedded magnetized portion located between an outside and an inside surface of a wall of the catheter 64, where the magnetized portion 65 extends around the entire circumference of the catheter 64. It is acceptable for the magnetized portion 65 to include an embedded magnetized portion that is located around less than an entirety of the circumference of the catheter 64, for example along a 180 degree arc around only a part of the circumference of the catheter 64.

FIG. 4B is a perspective view of a catheter 74 including a portion 75 that is magnetized. The portion 75 that is magnetized extends over substantially the entire length of the catheter and 74. The magnetized portion 75 includes an embedded magnetized portion located between an outside and an inside surface of a wall of the catheter 64, where the magnetized portion 75 extends around the entire circumference of the catheter 74. It is acceptable for the magnetized portion 75 to include an embedded magnetized portion that is located around less than an entirety of the circumference of the catheter 74, for example along a 180 degree arc around only a part of the circumference of the catheter 74.

FIG. 4C is a perspective view of a catheter 84 including a portion 85 that is magnetized. The portion 85 that is magnetized is wrapped in a spiral shape around the proximal end portion of the catheter 84. The spiral magnetized portion 85 is located between an outside and an inside surface of a wall of the catheter. The magnetized portion 85 is suitably embedded or molded into the wall of the catheter 84. The spiral nature of the magnetized portion 85 loops around the circumference of the catheter 84.

FIG. 5A is a cross-sectional view of the catheter 34 taken through the magnetized portion 55. The catheter 34 includes a tubular wall 90 having an inside surface 92 and an exterior (outside) surface 94. The magnetized portion 55 of the catheter 34 is located between the inside surface 92 and an exterior surface 94. The magnetized portion 55 encircles the entire circumference of the catheter 34. The cross-sectional view of FIG. 5A is taken at one segment along the catheter 34. In some embodiments the magnetized portion 55 extends the entire length of the catheter 34. In some embodiments the magnetized portion 55 is localized to a segment of less than about half of the length of the catheter 34.

FIG. 5B is a cross-sectional view of one embodiment of a catheter 104. The catheter 104 includes a tubular wall 110 including an inside surface 112 and an exterior surface 114. A magnetized portion 115 of the catheter 104 is located between the inside surface 112 and the exterior surface 114 and extends over and is localized to approximately half of the circumference of the catheter 104. During use, it is desirable to insert the catheter 104 into the urethra with the magnetized portion 115 oriented in a direction posterior relative to the urethra. In one embodiment, a visual indicator 120 is provided on the exterior surface 114 of the catheter 104 to indicate the location on the catheter 104 that includes the magnetized portion 115. For example, in one embodiment the visual indicator 120 is molded into the exterior surface 114 as a colored line. The magnetized portion 115 is located at least at a proximal portion of the catheter 104 and the visual indicator is located at least at a distal end of the catheter 104, which allows the surgeon to "see" the relative orientation of the magnetized portion 115. Inserting the catheter 104 into the urethra with the colored line 120 facing toward the spine of the patient (e.g., oriented in the posterior direction) ensures that the magnetized portion 115 will be located posterior relative to the urethra.

FIGS. 6-14 illustrate the use of the surgical system 30 and a method of dissecting tissue away from the posterior urethra.

Figure 6:
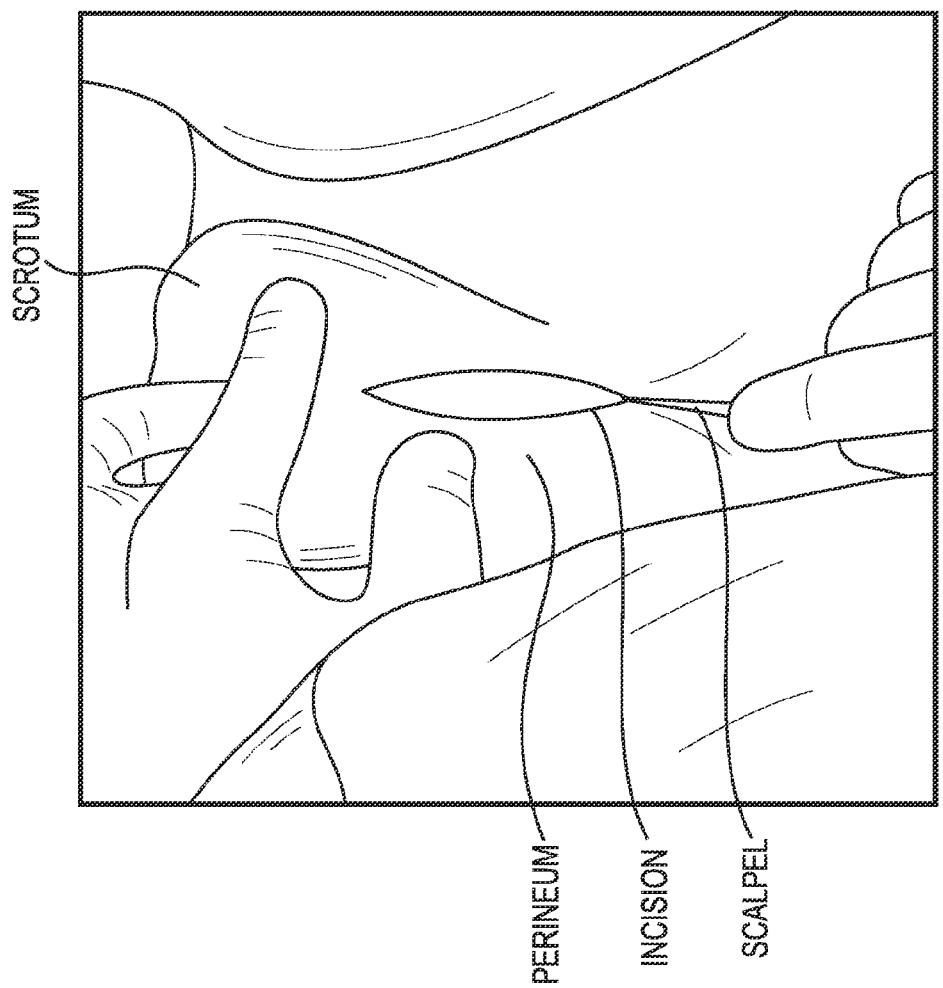

FIG. 6 is a schematic view of a male patient prepped for surgery. The catheter 34 has been inserted into the urethra. The patient is in a lithotomy position with the knees elevated above the head. The surgeon forms an incision in the perineum between the scrotum and the rectum.

Figure 7:
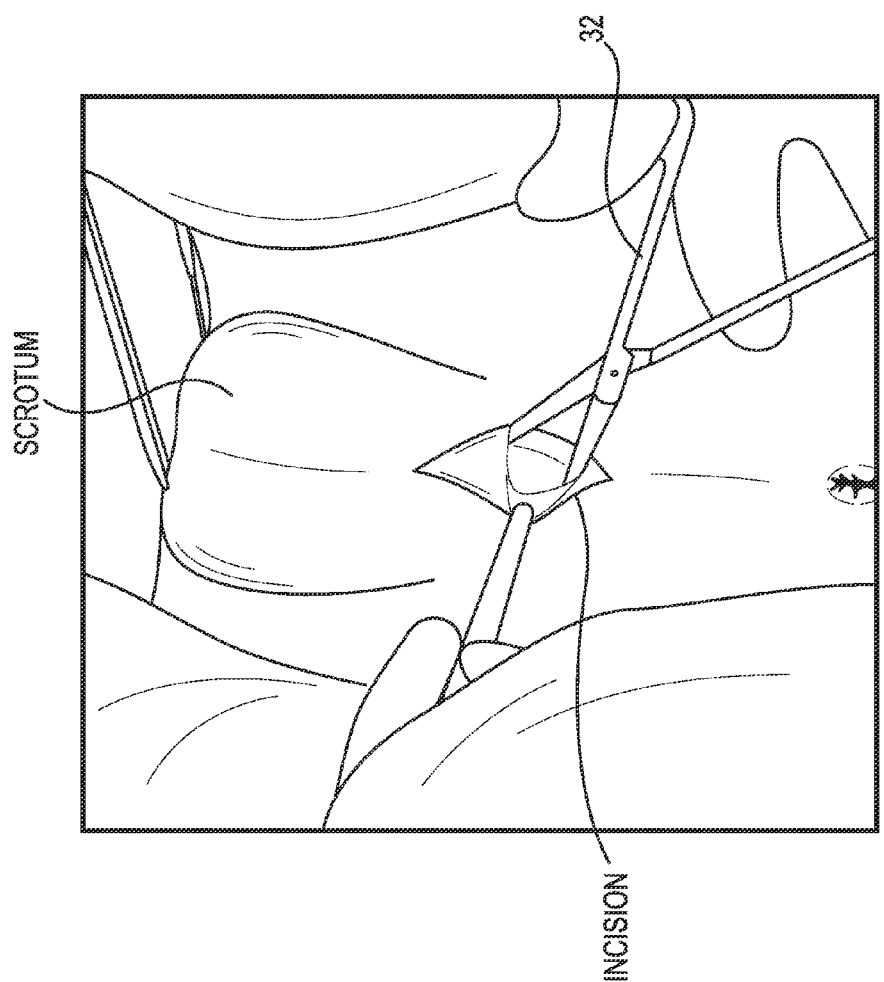

FIG. 7 is a schematic view of the surgeon using an instrument to dissect tissue to expose the bulbospongiosus muscle around the urethra. One suitable instrument is the tool 32 described above.

Figure 8:
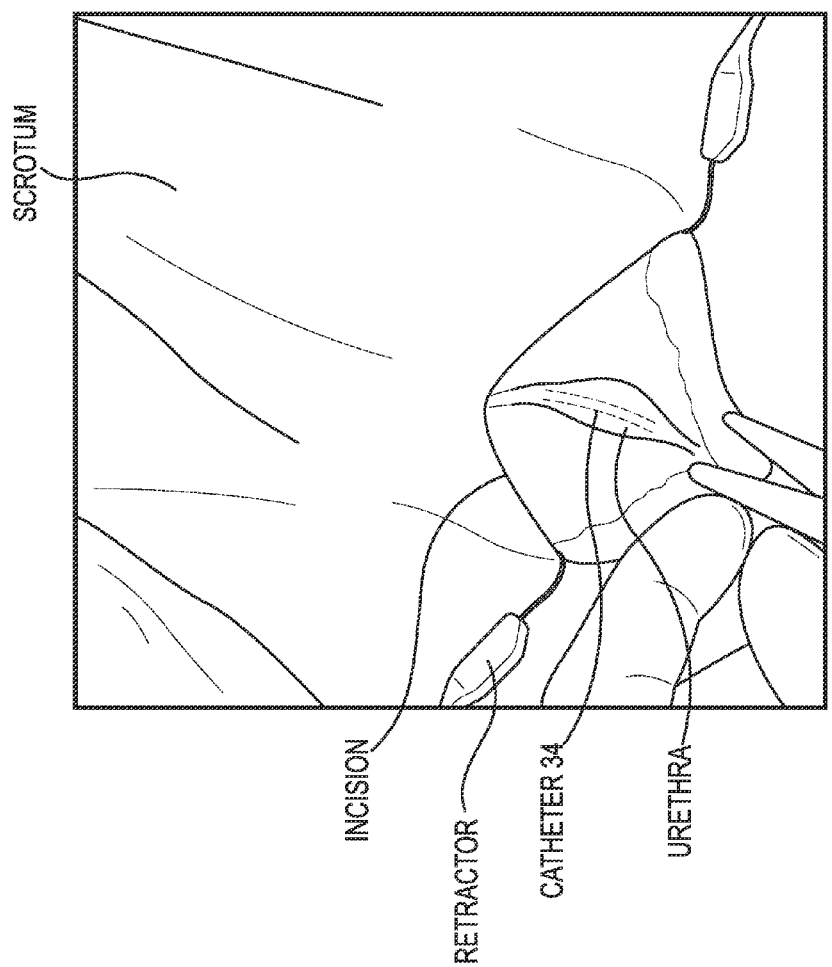

FIG. 8 is a schematic view of tissue dissected laterally relative to the incision. The fascia around the bulbospongiosus muscle has been dissected to expose a portion of the bulbar muscle and bulbar urethra for access by the surgeon.

Figure 9:
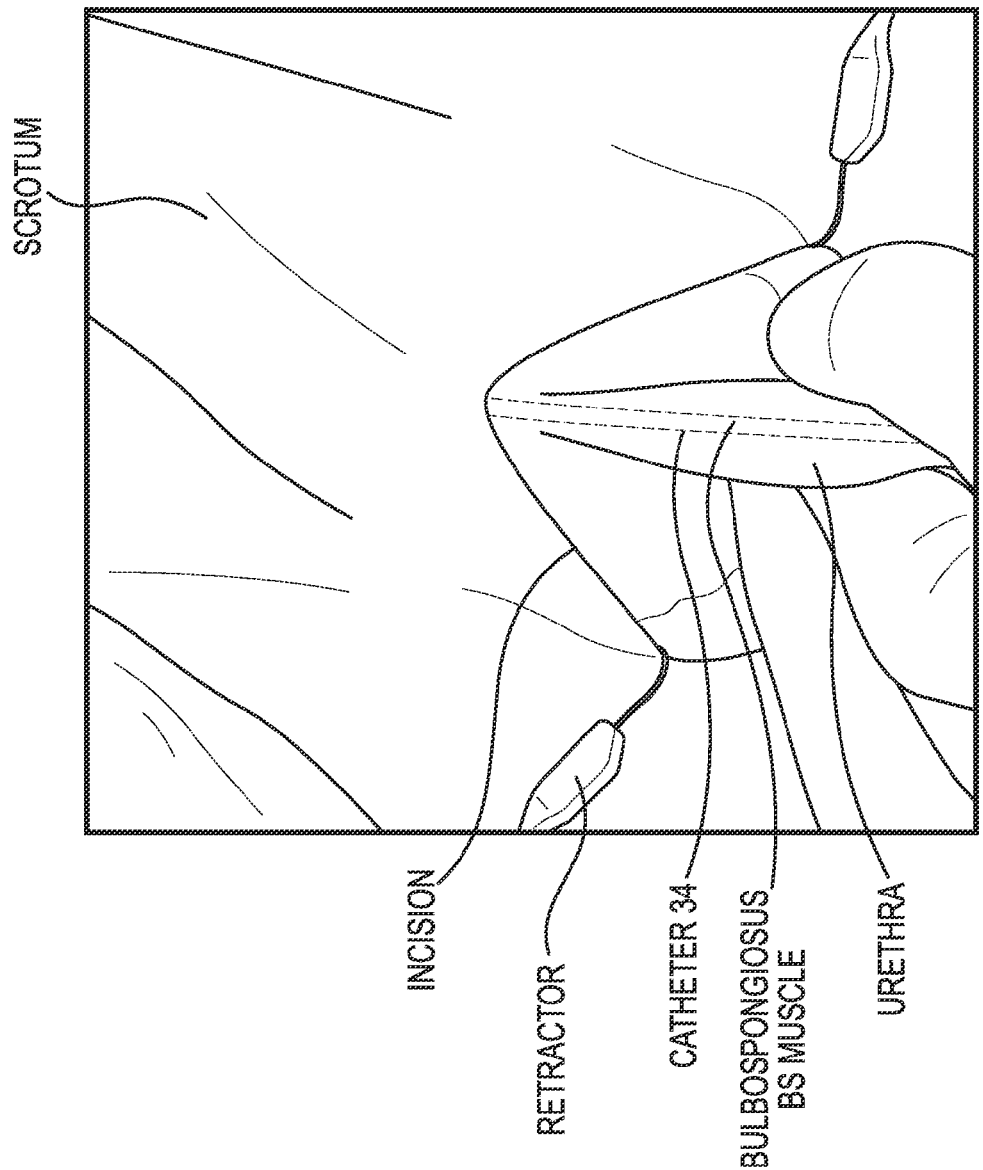

FIG. 9 is a schematic view of the urethra, and the bulbar muscle around the urethra, exposed and immobilized relative to the incision. The anterior portion of the urethra is visible to the surgeon. The catheter 34 is inside the urethra and the magnetized portion 55 is present within the urethra at least in the location of the bulbar urethra, posterior to the urethra. The surgeon is using his/her index finger and thumb to identify and immobilize the urethra and the muscle around the urethra.

Figure 10:
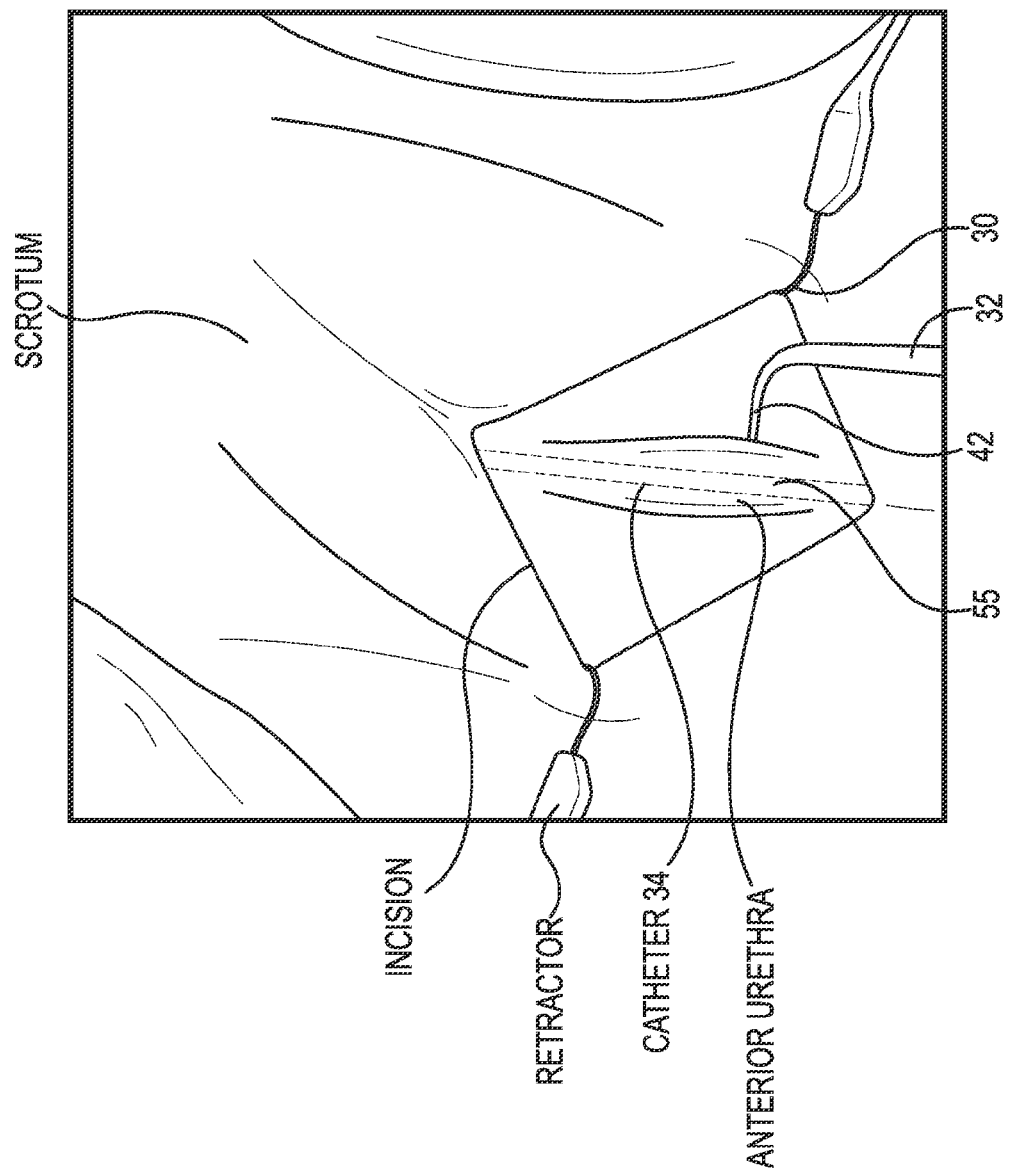

FIG. 10 is a schematic view of the surgical system 30 employed to dissect tissue posterior of the urethra. The tool 32 is used to dissect tissue around and behind the urethra. The cutting surface 42 of the tool 32 is magnetized to a first polarity. The catheter 34 is in the urethra and the magnetized portion 55 (also magnetized to the first polarity) is present on at least the posterior portion of the urethra. The tool is directed posterior of the urethra and the cutting surface 42 is operated to dissect tissue behind urethra. The magnetized portion 55 of the catheter 34 repels and pushes away the magnetized dissection head 42 of the tool 32 to reduce the likelihood of the dissection head 42 undesirably contacting urethra.

Figure 11:
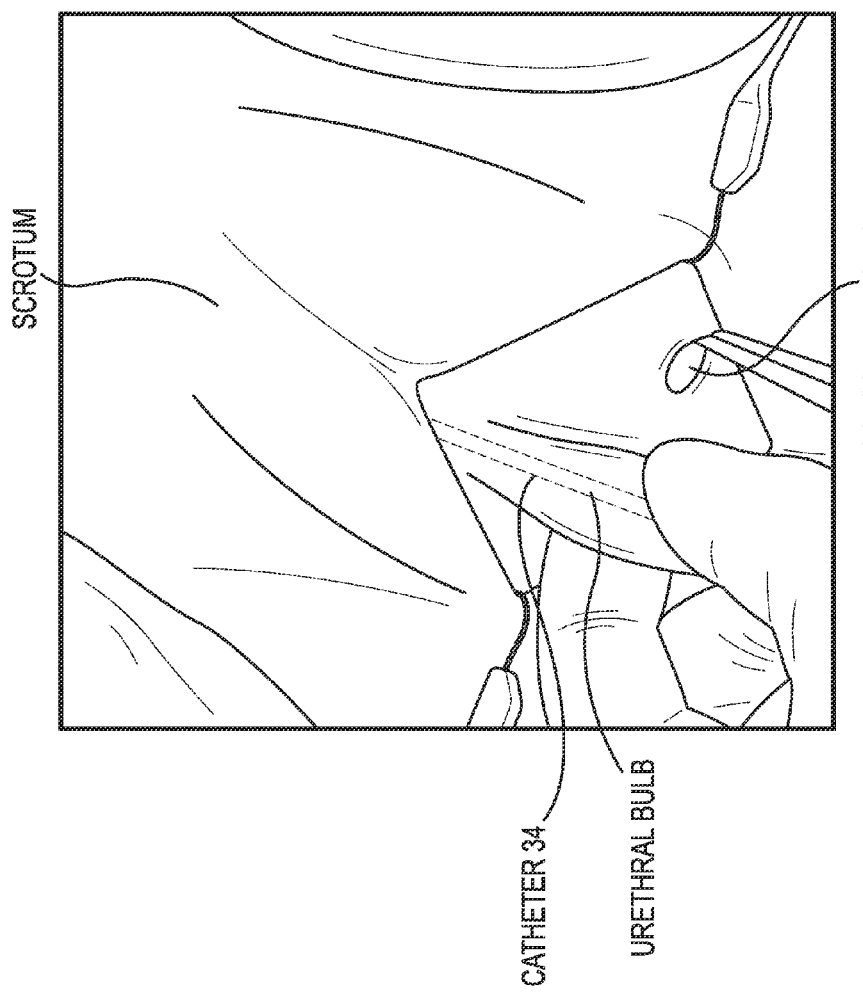

FIG. 11 is a schematic view of an access path formed by the surgical system 30 posterior of the urethra.

Figure 12:
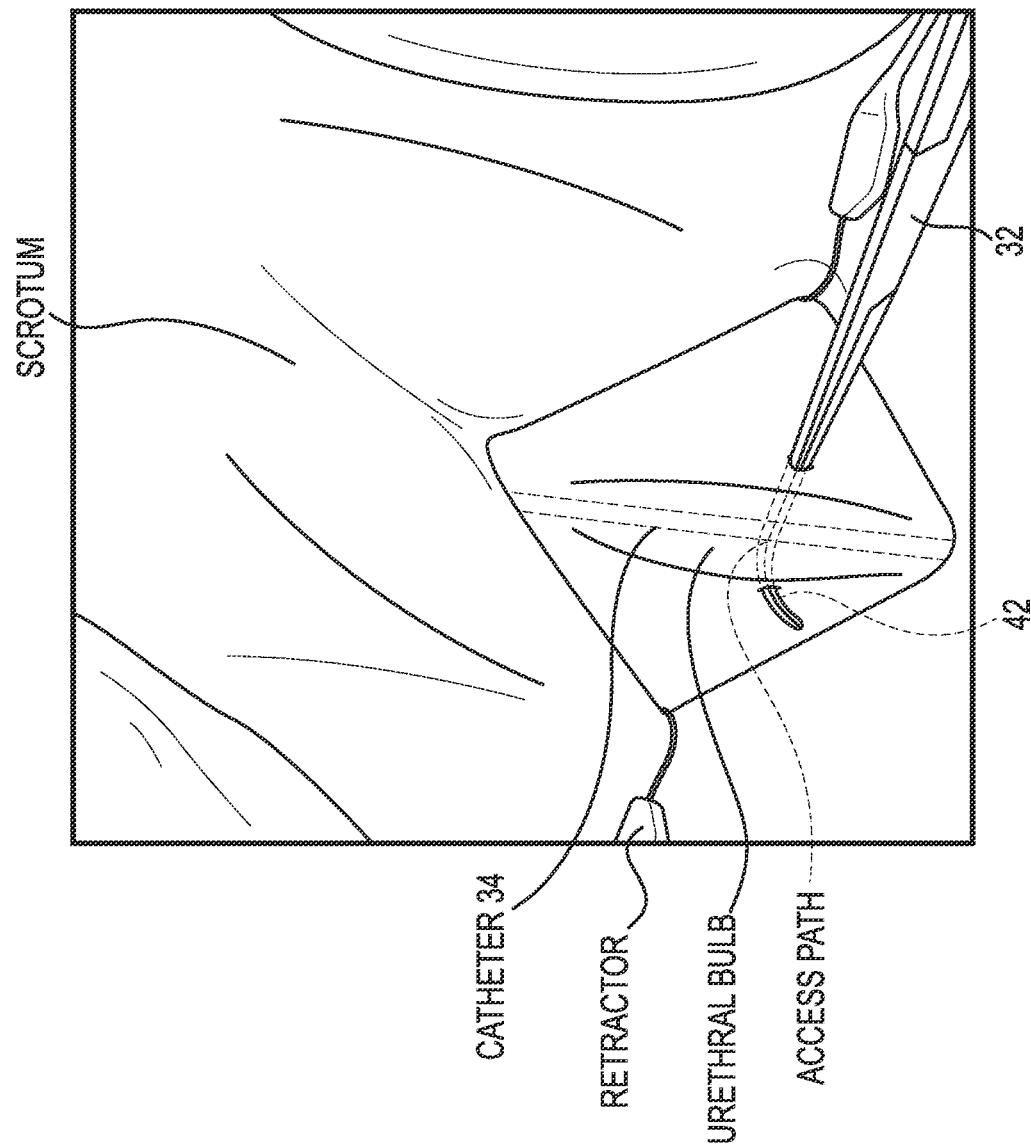

FIG. 12 is a schematic view of the tool 32 employed to identify the access path behind and posterior to the urethra. The surgeon uses the tool 32 to identify the access path and to ensure that the axis path is open on the backside or posterior side of the urethra. The inflatable cuff 22 will be directed through the access path behind and around the urethra.

FIG. 13 is a schematic view of a tab 150 of the cuff 22 inserted through the axis path behind and posterior to the urethra.

FIG. 14 is a schematic view of the cuff 22 placed around the urethra.

Embodiments provide a method of dissection tissue away from a urethra. The method includes, as described above, providing a tool 32 having a tissue dissection head 42 that is magnetized to a first polarity, and a catheter 34 having a repel portion 55 that is magnetized to a same polarity as the first polarity of the tissue dissection head 42. The method includes inserting the repel portion 55 of the catheter 34 into the urethra, and dissecting tissue away from the urethra with the tissue dissection head 42 and in so doing repelling the tissue dissection head 42 away from the repel portion 55 of the catheter 34 and away from the urethra.

The method additionally includes inflating a balloon 58 (FIG. 2) of the catheter 34 and locating the repel portion 55 of the catheter 34 in a bulbar urethral portion of the urethra.

The method additionally includes inserting the proximal portion 52 (FIG. 2) of the catheter 34 into a bladder and draining urine out of the bladder through the urethra.

The method additionally includes dissecting tissue away from a posterior side of the urethra and creating an open pathway around the urethra, as illustrated in FIG. 12.

The method additionally includes moving scissor portions of the tissue dissection head 42 and sizing the open pathway around the urethra to receive an artificial urinary sphincter, as illustrated in FIGS. 13-14.

The method additionally includes dissecting tissue away from a posterior side of the urethra with the tissue dissection head 42 obstructed from a line of sight of a user of the tissue dissection head.

FIG. 15 is a top view of one embodiment of a kit 200 of parts including the dissection tool 32, the catheter 34, and instructions 202 for use. The dissection tool and the catheter are suitably provided by any of the embodiments described in this application.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A surgical system adapted for dissection of tissue away from a body lumen, the surgical system comprising:
    a tool including a shaft connected between a handle and a tissue dissection head, with at least the tissue dissection head of the tool magnetized to a first polarity; and a catheter insertable into a urethra, with a portion of the catheter magnetized to the same polarity as the first polarity;

wherein, when the catheter is inserted into the urethra, the polarity of the catheter is configured to repel the first polarity of the tissue dissection head of the tool away from the catheter and away from the urethra;

wherein the portion of the catheter magnetized to the same polarity as the first polarity is located in an approximate 180 degree arc around the circumference of the catheter.

2. The system of claim 1, wherein the portion of the catheter magnetized to the same polarity as the first polarity is located between an inside surface and an outside surface of a tubular wall of the catheter.

3. The system of claim 1, wherein the portion of the catheter magnetized to the same polarity as the first polarity extends along less than half of a length of the catheter.

4. The system of claim 1, wherein the portion of the catheter magnetized to the same polarity as the first polarity extends between a balloon positioned at a proximal end of the catheter and a distal end of the catheter.

5. The system of claim 1, wherein the portion of the catheter magnetized to the same polarity as the first polarity is located in a region of less than an entirety of a circumference of the catheter.

6. The system of claim 1, wherein the catheter has a tubular wall with an inside surface and an outside surface, and the catheter includes a visual indicator formed in the tubular wall that is configured to indicate a location of the approximate 180 degree arc around the circumference of the catheter.

7. The system of claim 1, wherein the catheter includes a lumen that is adapted to transport urine through the catheter.

8. A kit of parts comprising:
a tool having a tissue dissection head that is magnetized to a first polarity;
a catheter insertable into a urethra, the catheter having a repel portion that is magnetized to the same polarity as the first polarity of the tissue dissection head to thus configure the repel portion of the catheter to maintain a separation distance away from the tissue dissection head;
wherein the repel portion of the catheter is located in an approximate 180 degree arc around the circumference of the catheter; and
instructions for use of the tool and the catheter.

9. The kit of parts of claim 8, wherein the repel portion is located in a wall of the catheter.

10. The kit of parts of claim 8, wherein the repel portion extends along an entire length of the catheter.

11. The kit of parts of claim 8, wherein the catheter includes a proximal portion that is insertable into the urethra and a distal portion that is configured to remain outside of the urethra, with the repel portion located in the proximal portion of the catheter, and the distal portion of the catheter includes a visual indicator provided to indicate a location of the repel portion of the catheter.

* * * * *